United States Patent [19]

Torii et al.

[11] 4,401,528
[45] Aug. 30, 1983

[54] PROCESS FOR PREPARING 2-OXYCEPHALOSPORIN DERIVATIVES

[75] Inventors: Sigeru Torii; Hideo Tanaka; Junzo Nokami; Takashi Shiroi, all of Okayama; Norio Saito, Tokushima; Michio Sasaoka, Okayama, all of Japan

[73] Assignee: Otsuka Kagaku Yakuhin Kabushiki Kaisha, Japan

[21] Appl. No.: 407,328

[22] Filed: Aug. 12, 1982

[30] Foreign Application Priority Data

Aug. 25, 1981 [JP] Japan .................... 56-133774

[51] Int. Cl.³ .................................. C25B 3/02
[52] U.S. Cl. ....................... 204/78; 204/59 R; 204/72
[58] Field of Search ............ 204/59 R, 72, 73 R, 204/78

[56] References Cited

U.S. PATENT DOCUMENTS 4,042,472  8/1977  Hall ............................ 204/73 R
4,219,393  8/1980  Torii et al. ...................... 204/78

Primary Examiner—F. Edmundson
Attorney, Agent, or Firm—Larson and Taylor

[57] ABSTRACT

This invention provides a process for preparing 2-oxycephalosporin derivative represented by the formula

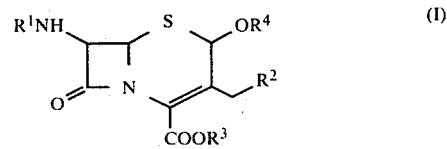

wherein $R^1$ represents hydrogen atom, acyl group, or lower alkoxycarbonyl group optionally substituted with halogen atom, $R^2$ represents hydrogen atom, halogen atom or acyloxy group optionally substituted with halogen atom, $R^3$ represents hydrogen atom, lower alkyl group optionally substituted with halogen atom, or phenyl-lower alkyl group which may be optionally substituted with nitro group, halogen atom or lower alkoxy group on the phenyl ring, and $R^4$ represents lower primary or secondary alkyl or lower alkylcarbonyl, the process comprising electrolytically oxidizing a cephalosporin derivative represented by the formula

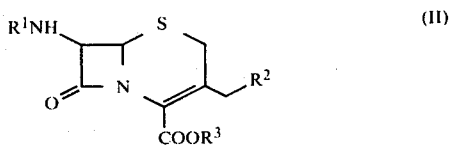

wherein $R^1$, $R^2$ and $R^3$ are as defined above, in the presence of a lower carboxylic acid or lower primary or secondary alcohol, and a supporting electrolyte.

8 Claims, No Drawings

PROCESS FOR PREPARING 2-OXYCEPHALOSPORIN DERIVATIVES

This invention relates to a process for preparing 2-oxycephalosporin derivatives and more particularly to a process for preparing 2-oxycephalosporin derivatives represented by the formula

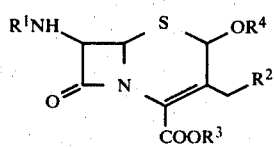

wherein $R^1$ represents hydrogen atom, acyl group or lower alkoxycarbonyl group optionally substituted with halogen atom, $R^2$ represents hydrogen atom, halogen atom or acyloxy group optionally substituted with halogen atom, $R^3$ represents hydrogen atom, lower alkyl group optionally substituted with halogen atom, or phenyl-lower alkyl group which may be substituted with nitro group, halogen atom or lower alkoxy group on the phenyl ring, and $R^4$ represents lower primary or secondary alkyl group or alkylcarbonyl group.

The 2-oxycephalosporin derivatives of the formula (I) prepared by the process of this invention are useful as the intermediates for preparing 2-substituted-cephalosporin-type antibiotics of the formula

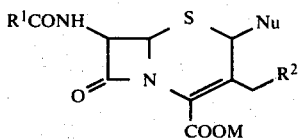

wherein $R^1$ and $R^2$ are as defined above, Nu represents methylthio, ethylthio or phenylthio, and M represents potassium or sodium.

The compounds of the formula (A) have antibacterial activity, and are especially useful for inhibitting gram-positive bacteria. The compounds of the formula (A) can be prepared from the compound of the formula (I) as schematically shown below

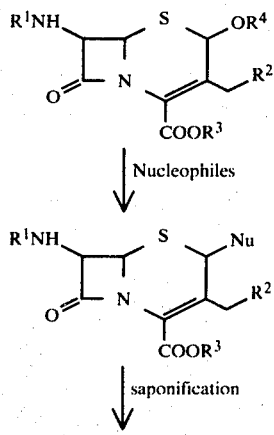

wherein $R^1$, $R^2$, M and Nu are as defined above.

Conventional processes for preparing 2-oxycephalosporin derivatives include, for example, (i) a process in which peracid is reacted with cephalosporin derivative of the formula

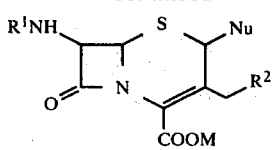

wherein $R^1$, $R^2$ and $R^3$ are as defined above to form the corresponding sulfoxide which is then converted to 2-acetoxy-cephalosporin derivative of the formula (I) by undergoing Pummerer rearrangement (D. O. Spry, Tetrahedron Lett., 1972, 3717), (ii) a process in which chorine, tert-butylhypochloride and N-chlorosuccinimide are reacted in an alcoholic solvent with the cephalosporin derivative of the formula (II), thereby giving 2-alkoxycephalosporin derivative of the formula (I) (J. Chem. Soc., (C), 1970, 340; D. O. Spry, Tetrahedron Lett., 1972, 3717; H. Yanagisawa et al, J. Antibiotics, 29, 969 (1976); C. U. Kim and D. N. McGregor, Tetrahedron Lett., 1978, 409), etc.

However, these processes have various drawbacks. For example, the process (i) requires two steps, involves extremely limited conditions for Pummerer rearrangement and entails complicated operations. The process (ii) requires stoichiometric amounts of chlorinating agent, consequently producing large amounts of by-products.

Furthermore, these conventional processes requires special cares in handling reagents and involve cumbersome procedures for the reaction and for the purification of the reaction product, hence commercially unfavorable.

An object of this invention is to provide a process for easily preparing the derivative of the formula (I) by a single step.

Another object of the invention is to provide a process for preparing the derivative of the formula (I) in high yields with small amounts of by-products involved.

Still another object of the invention is to provide a process for preparing the derivative of the formula (I) in commercially advantageous manner with use of reagents easy to handle by a simple procedure.

These objects and other features of the invention will become apparent from the following description.

This invention provides a process for preparing a 2-oxycephalosporin derivative of the formula

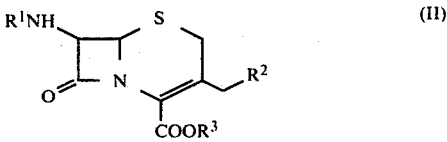

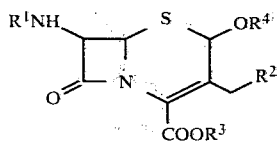

wherein $R^1$ represents hydrogen atom, acyl group, or lower alkoxycarbonyl group optionally substituted with halogen atom, $R^2$ represents hydrogen atom, halogen atom or acyloxy group optionally substituted with halogen atom, $R^3$ represents hydrogen atom, lower alkyl group optionally substituted with halogen atom, or phenyl-lower alkyl group which may optionally be substituted with nitro group, halogen atom or lower alkoxy group on the phenyl ring, and $R^4$ represents lower primary or secondary alkyl or lower alkylcarbonyl group, the process comprising electrolytically oxidizing a cephalosporin derivative of the formula

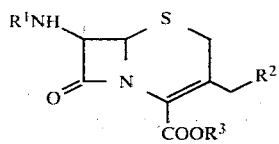

wherein $R^1$, $R^2$ and $R^3$ are as defined above, in the presence of a lower carboxylic acid or lower primary alcohol or lower secondary alcohol, and a supporting electrolyte.

We conducted extensive research to develop a commercially favored process for preparing 2-oxycephalosporin derivative of the formula (I). As a result, we have found that the 2-oxycephalosporin derivative of the formula (I) can be prepared in high yields by an extremely simple procedure of electrolytically oxidizing the cephalosporin derivative of the formula (II) in the presence of a lower carboxylic acid or lower primary or secondary alcohol, and a supporting electrolyte. We also found that this process employs reagents easy to handle, facilitates the separation and purification of the contemplated compound and produces extremely small amounts of by-products, hence commercially suitable for preparing the 2-oxycephalosporin derivative of the formula (I). This invention has been accomplished based on these novel findings.

Examples of the acyl groups represented by $R^1$ in the starting compound of the formula (II) are formyl, acetyl, propanoyl, chloroacetyl, phenylacetyl, phenoxyacetyl, p-chlorophenoxyacetyl, p-tolyloxyacetyl, benzoyl, p-chlorobenzoyl, etc. Examples of the lower alkoxycarbonyl groups optionally substituted with halogen atom are methoxycarbonyl, ethoxycarbonyl, n-propoxycarbonyl, isopropoxycarbonyl, n-butyloxycarbonyl, tert-butyloxycarbonyl, chloromethoxycarbonyl, bromomethoxycarbonyl, 2-chloroethoxycarbonyl, 2-bromoethoxycarbonyl, 2,2,2-trichloroethoxycarbonyl, 2,2,2-tribromoethoxycarbonyl, etc.

Examples of the halogen atoms represented by $R^2$ are chlorine, bromine, iodine atom, etc. Examples of the acyloxy groups optionally substituted with halogen atom are formyloxy, acetoxy, propanoyloxy, benzoyloxy, p-chlorobenzoyloxy, p-bromobenzoyloxy, etc.

Examples of the lower alkyl groups optionally substituted with halogen atom and represented by $R^3$ are methyl, ethyl, propyl, isopropyl, butyl, tert-butyl, 2-chloroethyl, 2-bromoethyl, 2,2,2-trichloroethyl, etc.

Examples of the phenyl-lower alkyl groups optionally substituted with nitro group, halogen atom or lower alkoxy group on the phenyl ring are benzyl, diphenylmethyl, triphenylmethyl, 2-phenylethyl, o-methoxybenzyl, p-nitrobenzyl, p-chlorobenzyl, p-methoxybenzyl, etc.

Examples of the lower primary or secondary alkyl groups represented by $R^4$ of the 2-oxycephalosporin derivative of the formula (I) are ethyl, methyl, n-propyl, isopropyl, n-, sec- or iso-butyl, etc. Examples of the lower alkylcarbonyl groups are formyl, acetyl, propanoyl, etc.

According to this invention, the compound of the formula (II) is electrolytically oxidized in lower carboxylic acid or lower primary or secondary alcohol. Useful lower carboxylic acids include formic acid, acetic acid, propionic acid, etc. Exemplary of useful lower primary or secondary alcohols are methanol, ethanol, n-propanol, isopropanol, n-butanol, isobutanol, sec-butanol, etc. This electrolytic oxidation gives 2-oxycephalosporin derivative of the formula (I) having —$OR^4$ group corresponding to the type of lower carboxylic acid or lower primary or secondary alcohol used. The amount of the lower carboxylic acid or lower primary or secondary alcohol, although not particularly limited, is about 5 to about 500 parts by weight, per part by weight of the starting cephalosporin derivative of the formula (II).

With this invention, appropriate inert solvent can be added to the lower carboxylic acid or lower primary or secondary alcohol. The inert solvent is used in an amount of about 1 to about 90% by volume based on the volume of the mixture. Useful inert solvents include a wide variety of known solvents which do not affect an electrolytic reaction, such as tert-butanol, tert-amyl alcohol and like tertiary alcohols; diethyl ether, dibutyl ether, 1,2-dimethoxyethane, tetrahydrofuran and like ethers; acetonitrile, butyronitrile and like nitriles; dichloromethane, chloroform, dichloroethane, dibromoethane, chlorobenzene and like halogenated hydrocarbons, etc.

With this invention, a supporting electrolyte is used. Useful supporting electrolytes include salts usually used in an electrolytic oxidation, such as ammonium formate, ammonium actate, tetraethylammonium formate, tetraethylammonium acetate, tetrapropylammonium acetate, tetrabutylammonium acetate, tetrabutylammonium tosylate, tetraethylammonium tosylate, tetrabutylammonium perchlorate, triethylbenzylammonium chloride and like ammonium or quaternary ammonium salts; alkali metal salts or alkaline earth metal salts of formic acid, acetic acid, propionic acid and like lower fatty acids, such as salts of lithium, sodium, potassium, magnesium, calcium, barium, etc.; and alkali metal salts of perchloric acid and like perhalogenic acids. When the reaction is conducted in the presence of the lower carboxylic acid, it is preferable to employ, as the supporting electrolyte, the metal salt of the same lower carboxylic acid as used. In this case, the salt of carboxylic acid may be formed by adding sodium hydroxide, potassium hydroxide, barium oxide, magnesium oxide, calcium oxide, etc. Although variable depending on the shape of the electrode and electrolytic cell etc., the preferred amount of the supporting electrolyte is usually a saturation amount.

While any electrode usually used in this field is usable, a platinum or carbon electrode is preferably employed. Although feasible at either controlled potential or constant applied-voltage, the electrolysis can be conducted by maintaining the current density, for example, in the range of about 1 to about 500 mA/cm$^2$, preferably about 3 to about 50 mA/cm$^2$. The required amount of electric charge is variable depending on the type of the reaction medium or the supporting electrolyte, etc. Usually, an electric charge of about 2 to about 50 F, preferably about 2 to about 15 F, is passed per mole of the compound of the formula (II). Although the temperature is suitably determined in the range of about −10° to about 60° C., the electrolysis is feasible above or below this range.

The 2-oxycephalosporin derivative of the formula (I) can be easily purified by usual column chromatography, recrystallization, etc.

This invention is described below in more detail with reference to examples in which Ph means phenyl and Ac represents acetyl.

EXAMPLE 1

Synthesis of methyl ester of (6R, 7S)-2-acetoxy-7-phenoxyacetamidodeacetoxycephalosporanic acid

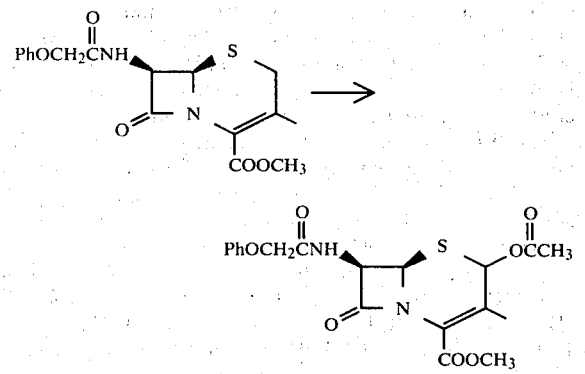

A 0.15 g quantity of lithium acetate was dissolved in 4 ml of acetic acid. To the solution was added 0.3 g of methyl ester of 7-phenoxyacetamidodeacetoxycephalosporanic acid. Using carbon electrodes (2 cm$^2$), electrolysis was continued for about 18 hours at constant current of 5 mA, at 4 V and at 20° C. Thereafter the reaction mixture was extracted with methylene chloride or chloroform. The extract was washed with sodium bicarbonate aqueous solution and dried over anhydrous sodium sulfate. The solvent was removed, and a light yellow liquid (0.32 g) was produced. The liquid was subjected to silica gel column chromatography using a 1:1 ethyl acetate-hexane mixture as a developer, giving 0.31 g of the contemplated compound. Yield 89%.

(IR) 3350, 1780, 1740, 1730, 1685 cm$^{-1}$.

(NMR) δ 2.05 (3H, s), 2.08 (3H, s), 3.77 (3H,s), 4.46 (2H, s), 5.05 (1H, d, J=5 Hz), 5.81 (1H, d-d, J=9 and 5 Hz), 6.22 (1H, s), 6.7–7.4 (5H, m), 7.58 (1H, d, J=9 Hz).

The same procedure as above was repeated by using the following salts of acetic acids, producing the contemplated compounds in the yields shown below.

| Salt of acetic acid | Yield |
|---|---|
| AcONa | 80% |
| (AcO)$_2$Mg | 87% |
| (AcO)$_2$Ba | 89% |

EXAMPLE 2

Synthesis of trichloroethyl ester of (6R, 7S)-2-acetoxy-7-phenoxyacetamidodeacetoxycephalosporanic acid

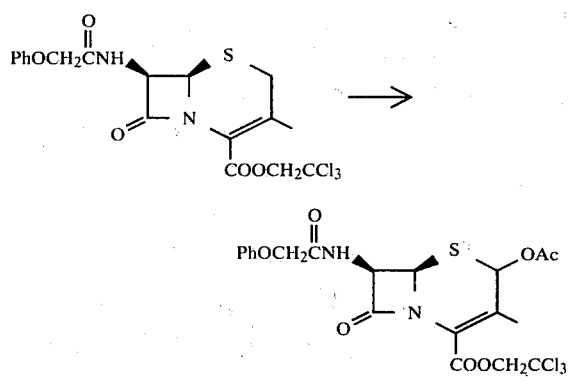

0.6 g of barium acetate was dissolved in 6 ml of acetic acid and 4 ml of tert-butyl alcohol. To the solution was added 0.1 g of trichloroethyl ester of 7-phenoxyacetamidodeacetoxycephalosporanic acid. Using carbon electrodes (2 cm$^2$), electrolysis was continued for about 4.5 hours at constant current of 5 mA, at 4 V, and at 20° C. The same subsequent procedure as in Example 1 was repeated, affording 0.091 g of the contemplated compound. Yield 82%.

(NMR) δ 2.10 (6H, s), 4.47 (2H,s), 4.83 (2H, ABq, J=3 Hz) 5.10 (1H, d, J=5 Hz), 5.88 (1H, d-d, J=9 and 5 Hz), 6.21 (1H, d, J=9 Hz), 6.6–7.4 (5H, m).

EXAMPLE 3

Synthesis of benzyl ester of (6R, 7S)-2-acetoxy-7-phenoxyacetamidodeacetoxycephalosporanic acid

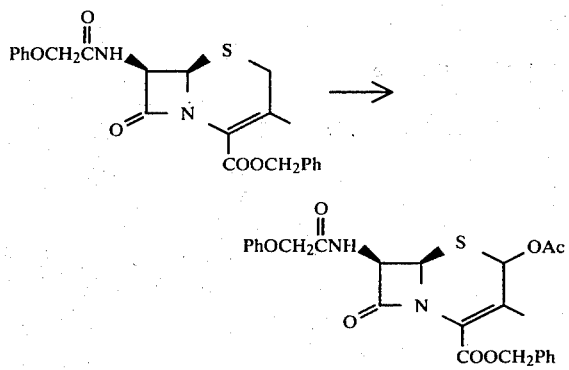

30 mg of magnesium oxide was dissolved in 2.3 ml of acetic acid. To the solution was added 200 mg of benzyl ester of 7-phenoxyacetamidodeacetoxycephalosporanic acid. Electrolysis was continued for about 9.5 hours at constant current of 5 mA, at 4 V, and at 20° C. to 25° C. The subsequent procedure as in Example 1 was repeated producing 186 mg of the contemplated compound. Yield 82%.

(IR) 3450, 1790, 1745, 1730, 1690 cm$^{-1}$.

(NMR) δ 1.98 (3H, s), 2.00 (3H, s), 4.40 (2H, s), 5.00 (1H, d, J=5 Hz), 5.16 (2H, s), 5.76 (1H, d-d, J=9 and 5 Hz), 6.17 (1H, s), 6.6–7.4 (11H, m).

EXAMPLE 4

Synthesis of nitro-benzyl ester of (6R, 7S)-2-acetoxy-7-phenoxyacetamidodeacetoxycephalosporanic acid

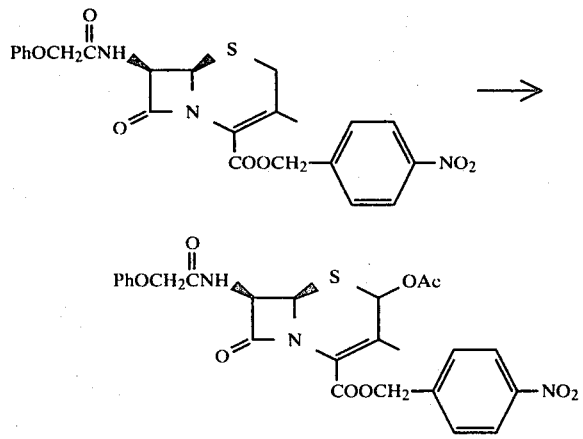

0.5 g of barium acetate was dissolved in 6 ml of acetic acid. To the solution was added 0.5 g of the starting material. Using carbon electrodes (4 cm$^2$), electrolysis was continued for 22 hours at constant current of 5 mA, at 4 V, and at 10° C. to 15° C. The same subsequent procedure as in Example 1 was repreated, giving 0.46 g of the contemplated compound. Yield 82%.

(IR) 3350, 1770, 1730, 1680, 1340 cm$^{-1}$.

(NMR) δ 2.00 (6H, s), 4.42 (2H, s), 5.02 (1H, d, J=5 Hz), 5.22 (2H, s), 5.80 (1H, d-d, J=9 and 5 Hz), 6.19 (1H, s), 6.60–7.40 (6H, m), 7.75 (4H, q).

EXAMPLE 5

Synthesis of benzyl ester of (6R, 7S)-2-acetoxy-7-phenylacetamidodeacetoxycephalosporanic acid

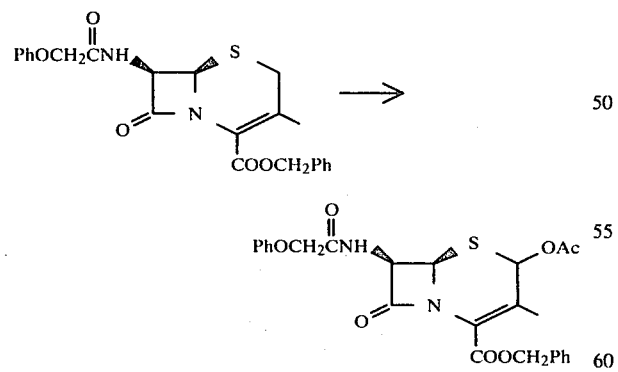

30 mg of magnesium oxide was dissolved in 2.5 ml of acetic acid. To the solution was added 200 mg of the starting material. Electrolysis was continued for about 10 hours at constant current of 5 mA, at 4 V, and at 20° C. to 25° C. The same subsequent procedure as in Example 1 was repeated, giving 194 mg of the contemplated compound. Yield 85%.

(IR) 3450, 1791, 1745, 1732, 1690 cm$^{-1}$.

(NMR) δ 1.98 (3H, s), 2.00 (3H, s), 3.61 (2H, s), 5.10 (2H, s), 5.00 (1H, d, J=5 Hz), 5.76 (1H, d-d, J=9 and 5 Hz), 6.17 (1H, s), 7.2–7.4 (11H, m).

EXAMPLE 6

Synthesis of benzyl ester of (6R,7S)-2-methoxy-7-phenoxyacetamidodeacetoxycephalosporanic acid

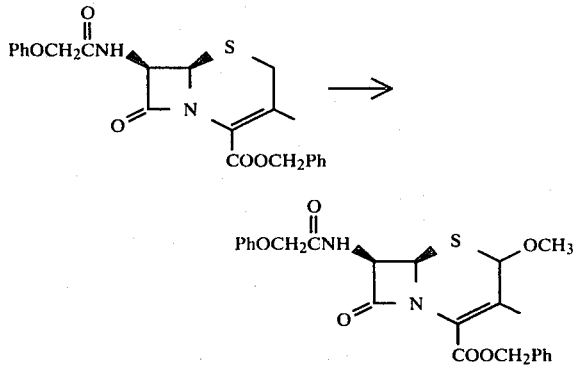

60 mg of triethylbenzylammoniumchloride was dissolved in a mixture of 1.5 ml methanol and 1.5 ml of chloroform. Thereto was added 100 mg of benzyl ester of 7-phenoxyacetamidodeacetoxycephalosporanic acid. Using platinum electrodes (1 cm$^2$), electrolysis was continued for about 4.3 hours at constant current of 5 mA, at 3 to 4 V, and at −10° C. Thereafter the reaction mixture was washed with water and extracted with chloroform. The extract was treated in the same manner as in Example 1, giving 85 mg of the contemplated compound. Yield 80%.

(IR) 3250, 1775, 1730, 1675 cm$^{-1}$.

(NMR) δ 2.14 (3H, s), 3.38 (3H,s), 4.49 (2H, s), 4.70 (1H, s), 4.96 (1H, d, J=5 Hz), 5.20 (2H, s), 5.80 (1H, d-d, J=9 and 5 Hz), 6.7–7.4 (10H, m), 7.45 (1H, d, J=9 Hz).

EXAMPLE 7

Synthesis of methyl ester of (6R, 7S)-2-isopropoxy-7-phenoxyacetamidodeacetoxycephalosporanic acid

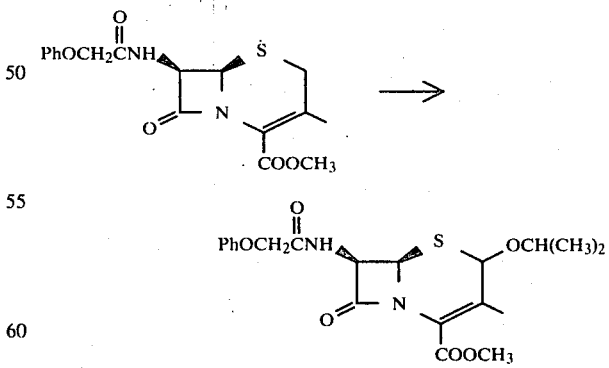

40 mg of tetraethylammoniumtosylate was dissolved in a mixture of 1.2 ml of chloroform and 1.2 ml of isopropyl alcohol. To the solution was added 100 mg of the starting material. Using platinum electrodes (1 cm$^2$), electrolysis was continued for about 6 hours at constant current of 5 mA, at 5 to 6 V and at 10° to 15° C. The resulting reaction mixture was treated in the same manner as in Example 6, affording 88.3 mg of contemplated compound. Yield 81.5%.

(IR) 3250, 1775, 1730, 1675 cm$^{-1}$.

(NMR) δ 1.08 (6H, d, J=7 Hz), 2.00 (3H, s), 3.70 (3H,s), 3.90 (1H, m), 4.39 (2H, s), 4.78 (1H, s), 4.95 (1H, d, J=5 Hz), 5.76 (1H, d-d, J=9 and 5 Hz), 6.6–7.3 (6H, m).

EXAMPLE 8

Synthesis of methyl ester of (6R, 7R)-2-acetoxy-7-phenoxyacetamidodeacetoxycephalosporanic acid

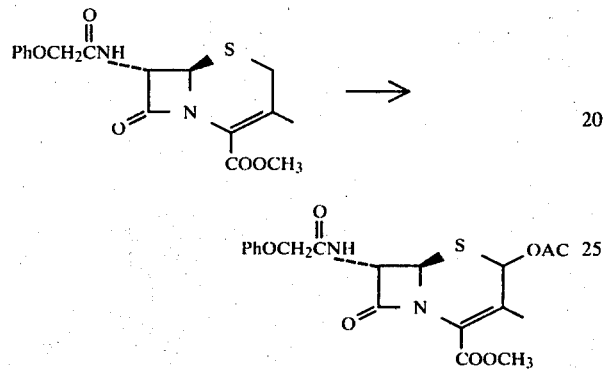

Methyl ester of (6R, 7R)-7-phenoxyacetamidodeacetoxycephalosporanic acid (0.3 g) was electrolyzed in the same manner as in Example 1, producing 0.306 g of the contemplated compound. Yield 87%.

(IR) 3400, 1780, 1740, 1675 cm$^{-1}$.

(NMR) δ 1.93 (3H, s), 2.05 (3H, s), 3.82 (3H, s), 4.45 (2H, s), 4.80 (1H, d, J=2 Hz), 4.88 (1H, d-d, J=2 and 8 Hz), 6.13 (1H, s), 6.7–7.5 (6H, m).

EXAMPLE 9

Synthesis of benzyl ester of (6R, 7R)-2-acetoxy-7-phenoxyacetamidodeacetoxycephalosporanic acid

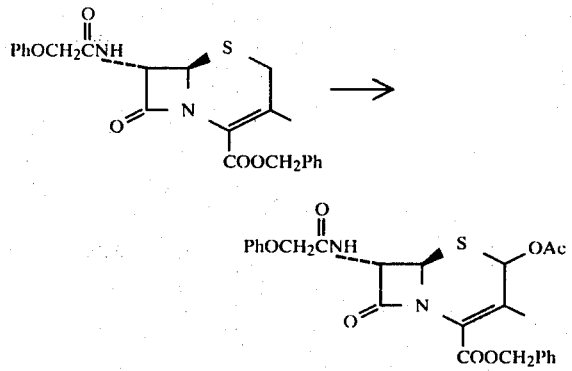

Benzyl ester of (6R, 7R)-7-phenoxyacetamidodeacetoxycephalosporanic acid (200 mg) was electrolyzed in the same manner as in Example 3, producing 203 mg of the contemplated compound. Yield 89%.

(IR) 3400, 1780, 1735, 1685 cm$^{-1}$.

(NMR) δ 1.91 (3H, s), 2.04 (3H, s), 3.48 (2H, s), 4.80 (1H, d, J=2 Hz), 5.00 (1H, d-d, J=2 and 9 Hz), 5.28 (2H, s), 6.18 (1H, s), 6.2–7.4 (11H, m).

EXAMPLE 10

Synthesis of methyl ester of (6R, 7S)-2-acetoxy-7-phenoxyacetamidocephalosporanic acid

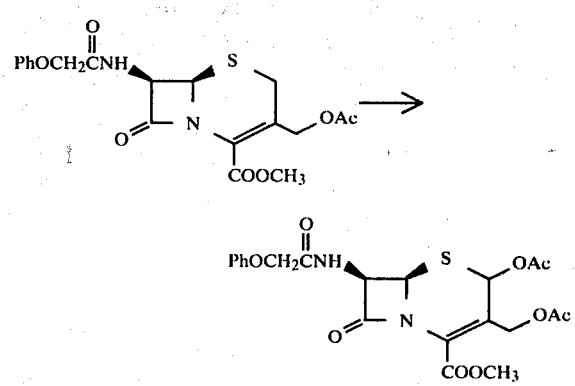

Methyl ester of 7-phenoxyacetamidocephalosporanic acid (200 mg) was electrolyzed in the same manner as in Example 1, giving 192 mg of the contemplated compound. Yield 90%.

(IR) 3350, 1790, 1735, 1690 cm$^{-1}$ (NMR) δ 2.05 (3H, s), 2.10 (3H, s), 3.91 (3H,s), 4.55 (2H, s), 4.98 (2H, ABq, J=13 Hz), 6.22 (1H, d, J=5 Hz), 6.01 (1H, d-d, J=14 and 5 Hz), 6.8–7.5 (6H, m).

We claim:

1. A process for preparing 2-oxycephalosporin derivative represented by the formula

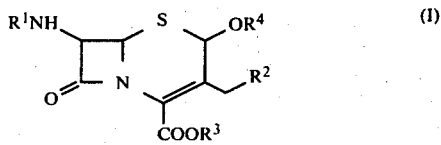

wherein $R^1$ represents hydrogen atom, acyl group, or lower alkoxycarbonyl group optionally substituted with halogen atom, $R^2$ represents hydrogen atom, halogen atom or acyloxy group optionally substituted with halogen atom, $R^3$ represents hydrogen atom, lower alkyl group optionally substituted with halogen atom, or phenyl-lower alkyl group which may be optionally substituted with nitro group, halogen atom or lower alkoxy group on the phenyl ring, and $R^4$ represents lower primary or secondary alkyl or lower alkylcarbonyl, the process comprising electrolytically oxidizing a cephalosporin derivative represented by the formula

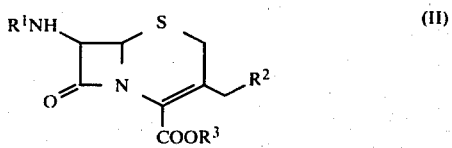

wherein $R^1$, $R^2$ and $R^3$ are as defined above, in the presence of a lower carboxylic acid or lower primary or secondary alcohol, and a supporting electrolyte.

2. A process as defined in claim 1 in which the lower carboxylic acid is formic acid, acetic acid or propionic acid.

3. A process as defined in claim 1 in which the lower primary or secondary alcohol is methanol, ethanol, n-propanol, isopropanol, n-butanol, isobutanol or sec-butanol.

4. A process as defined in claim 1 in which the lower carboxylic acid or lower primary or secondary alcohol is used in an amount of about 5 to about 500 parts by weight per part by weight of the cephalosporin compound of the formula (II).

5. A process as defined in claim 1 in which the electrolyte is ammonium or quaternary ammonium salt, alkali metal salt or alkaline earth metal salt of lower carboxylic acid or alkali metal salt of perhalogenic acid.

6. A process as defined in claim 1 in which the electrolysis is conducted at a current density of about 1 to about 500 mA/cm$^2$.

7. A process as defined in claim 1 in which an electric charge of about 2 to about 50 F per mole of the compound of the formula (II) is passed.

8. A process as defined in claim 1 in which the electrolysis is conducted at a temperature of about $-10°$ to about 60° C.

* * * * *